United States Patent [19]

Papenfuhs et al.

[11] Patent Number: 5,571,934
[45] Date of Patent: Nov. 5, 1996

[54] PROCESS FOR PREPARING SOLUTIONS OF POLYHYDROXY-FATTY ACID AMIDES HAVING GOOD COLOR QUALITY, AND THEIR USE

[75] Inventors: Bernd Papenfuhs, Neuötting; Reinhard Vybiral, Burgkirchen, both of Germany

[73] Assignee: Hoechst AG, Germany

[21] Appl. No.: 509,765

[22] Filed: Aug. 1, 1995

[30] Foreign Application Priority Data

Aug. 2, 1994 [DE] Germany .......................... 44 27 301.0

[51] Int. Cl.⁶ ........................ C07C 231/22; C07C 231/24
[52] U.S. Cl. ............................ 554/70; 554/187; 554/188; 554/69; 554/68; 554/66
[58] Field of Search ................................ 554/66, 70, 68, 554/69, 187, 188

[56] References Cited

FOREIGN PATENT DOCUMENTS

| 919428 | 2/1963 | United Kingdom . |
|---|---|---|
| 92/06073 | 4/1992 | WIPO . |
| 93/09215 | 5/1993 | WIPO . |
| 09215 | 8/1993 | WIPO . |
| 94/10130 | 5/1994 | WIPO . |

*Primary Examiner*—Gary Geist
*Assistant Examiner*—Deborah D. Carr
*Attorney, Agent, or Firm*—Connolly & Hutz

[57] ABSTRACT

Process for preparing solutions of polyhydroxy-fatty acid amides having good color quality In the process described, at least one sulfur compound from the group of dithionous acid is added in an active amount to the crude solutions, which are in general more or less brown in color, after which water-clear polyhydroxy-fatty acid amide products result.

10 Claims, No Drawings

PROCESS FOR PREPARING SOLUTIONS OF POLYHYDROXY-FATTY ACID AMIDES HAVING GOOD COLOR QUALITY, AND THEIR USE

BACKGROUND OF THE INVENTION

1. Field of the Invention

The invention relates to a process for preparing solutions, of improved color, of polyhydroxy-fatty acid amide which has been obtained by reaction of N-alkylpolyhydroxyamine and fatty acid alkyl ester. The invention furthermore relates to the use of these solutions.

2. Description of the Prior Art

Polyhydroxy-fatty acidamides are valuable surface-active compounds which can be employed for many uses. They can thus be employed, for example, as such or as a mixture with anionic, cationic and/or nonionic surfactants as cleaning agents, detergents, textile treatment agents and the like, and in particular in the form of solid products (for example as powders, grains or granules), solutions, dispersions, emulsions, pastes and the like. Since polyhydroxy-fatty acid amides are also readily biologically degradable and can be prepared from regenerating raw materials, they have recently acquired relatively great importance.

The polyhydroxy-fatty acid amides in question are as a rule compounds of the formula R—CO—NR'—Z, in which R is a hydrocarbon radical having about 5 to 30 carbon atoms, preferably 8 to 18 carbon atoms, R' is H, alkyl or hydroxyalkyl having up to preferably 8 carbon atoms and Z is a polyhydroxy hydrocarbon radical having at least three OH, which can also be alkoxylated, preferably a sugar alcohol radical. The preferred polyhydroxy-fatty acid amides thus correspond to the following formula $$\begin{array}{c} R^1-N-CO-R^2 \\ | \\ CH_2 \\ | \\ (CHOH)_n \\ | \\ CH_2OH \end{array}$$

in which $R^1$ is a short-chain alkyl, such as $C_1$ to $C_4$-alkyl, or hydroxyalkyl, such as —$CH_2CH_2OH$, $R^2$ is a fatty alkyl and n is 3 or 4. The compounds where n=4, which are particularly preferred, are called glycamides, and in the case of glucose as the hexose radical, glucamides. The fatty acid alkyl esters are in general fatty acid $C_1$ to $C_4$-alkyl esters, methyl, ethyl, propyl or isopropyl being preferred. The fatty acid methyl esters are particularly preferred. The fatty acid radical (the acyl group) in general has 6 to 24 carbon atoms, preferably 8 to 18 carbon atoms. It can be saturated or unsaturated (preferably mono- to tri-unsaturated).

Polyhydroxy-fatty acid amides are in general prepared by reaction of an N-alkylpolyhydroxyamine (for example N-alkylglucamine) with a fatty acid alkyl ester in the presence of basic catalysts, the reaction being carried out in the melt (in bulk) or with the aid of solvents. The following reaction equation with N-methylglucamine and lauric acid methyl ester is intended to illustrate this in more detail:

$$\begin{array}{c} CH_3-N-H \\ | \\ CH_2 \\ | \\ (CHOH)_4 \\ | \\ CH_2OH \end{array} + C_{11}H_{23}COOCH_3 \longrightarrow$$

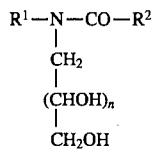

-continued $$\begin{array}{c} CH_3-N-CO-C_{11}H_{23} \\ | \\ CH_2 \\ | \\ (CHOH)_4 \\ | \\ CH_2OH \end{array} + CH_3OH$$

It is generally preferable to carry out the reaction in the presence of solvents.

Such preparation processes are described in a number of publications, of which WO 92/06073 and WO 94/10130 may be mentioned here as representative. The N-alkylpolyhydroxyamine and the fatty acid alkyl ester are employed in an essentially equimolar amount. The reaction is carried out at a temperature of up to about 135° C. Basic catalysts which are employed are, preferably, alkali metal hydroxides, alkali metal carbonates and/or $C_1$ to $C_4$ alkali metal alkoxides, such as sodium methylate and potassium methylate, and solvents which are employed are $C_1$- to $C_4$-alcohols, glycerol and/or glycols, such as ethylene glycol and propylene glycol (1,2-propylene glycol and 1,3-propylene glycol). The amount of catalyst is 0.1 to 20 mol %, based on the fatty acid ester. The solvent is employed in an amount such that the resulting solution of polyhydroxy-fatty acid amide is 10 to 80% strength by weight. If the solvent is expediently removed using a vacuum, the polyhydroxy-fatty acid amide is obtained in solid form, for example as a powder. The resulting polyhydroxy-fatty acid amide products, whether in solid form or in the form of solutions, do not have the desired color quality, and rather they are in general pale brown to dark brown in color.

There may also be mentioned as prior art the publication WO 93/09215, in which liquid color-stabilized detergent formulations are described, including, inter alia, those comprising polyhydroxy-fatty acid amides. Protection against a change in color of the fresh formulations is achieved by adding to the formulations 0.001 to 10% by weight, based on the total formulation, of one or more of the following color-stabilizing compounds: sulfites, hydrogen sulfites or pyrosulfites, sulfur dioxide, sulfurous acid, α-hydroxyalkylsulfonic acids, mercaptoethanol, sodium mercaptoacetate, 2-aminoethanethiol, cysteine, polycysteine, glutathione and formamidinesulfinic acid.

SUMMARY OF THE INVENTION

The object of the present invention is to brighten the more or less brown-colored polyhydroxy-fatty acid amides, i.e. to convert them into practically colorless products, in general prepared in the form of solutions from N-alkylpolyhydroxyamines and fatty acid esters by known processes.

It has been found, surprisingly, that polyhydroxy-fatty acid amides of good color quality are obtained if dithionous acid and/or derivatives thereof are incorporated into the product to be decolorized (crude product). This is an unexpected result, since—as comparison examples described later show—the effect sought is not achieved with other sulfur compounds which likewise have a reducing action, for example with those recommended in the abovementioned WO 93/09215. It was in fact not foreseeable that polyhydroxy-fatty acid amide can be improved in color to a high degree precisely and only with sulfur compounds from the group of dithionous acid.

DETAILED DESCRIPTION OF THE PREFERRED EMBODIMENT

The process according to the invention for preparing a polyhydroxy-fatty acid amide solution of improved color from N-alkylpolyhydroxyamine and fatty acid alkyl ester accordingly comprises mixing at least one sulfur compound from the group of dithionous acid into the crude solution in an active amount.

Preferred compounds from the group of dithionous acid are dithionous acid itself ($H_2S_2O_4$) and salts thereof, which can be primary in nature (acid salts) or secondary in nature. The salts include, for example, ammonium salts, alkanolammonium salts and metal salts, preferably of alkali metals and alkaline earth metals. Particularly preferred compounds are the ammonium dithionites and alkali metal dithionites, such as potassium dithionite and sodium dithionite. The sulfur compounds can be employed as such or in the form of a solution, preferably as an aqueous or aqueous/alcoholic ($C_1$ to $C_3$-alkanol) 10 to 50% strength by weight solution.

The amount of sulfur compound to be employed according to the invention can vary within wide limits. Because of the unexpectedly high activity, the bleaching effect sought is often also achieved even with very little dithionite compound. The active amount of compounds to be employed according to the invention is accordingly in general 0.005 to 1% by weight, preferably 0.05 to 0.15% by weight, the percentages by weight being based on the solution to be bleached.

The solutions to be treated according to the invention—as already mentioned—are as a rule those which are obtained in the preparation of polyhydroxy-fatty acid amides by reaction of alkylpolyhydroxyamines with fatty acid esters and are more or less brown in color. Those solutions which are obtained by dissolving impure (colored) polyhydroxy-fatty acid amide can also be treated according to the invention. The solvent preferably comprises water, a lower alcohol, such as $C_1$ to $C_4$-alkanol, a lower glycol, such as ethylene glycol and propylene glycol, or glycerol or a mixture thereof, for example a mixture of water and alcohol, water and glycol, alcohol and glycol or water, alcohol and glycol. The solutions to be purified in general comprise 10 to 80% by weight of polyhydroxy-fatty acid amide, preferably 20 to 60% by weight, based on the weight of the solution. The solutions are as a rule neutral or alkaline. Their pH is thus in general in the range from about 6 to 12, preferably from about 7 to 11.

The sulfur compounds described are added according to the invention to the solutions to be decolorized, expediently while stirring and while maintaining the pH values mentioned, a pH of 7 to 11 being preferred. The mixing in can be carried out at room temperature or an elevated temperature, i.e. in the range from about 20° to 100° C., preferably 40° to 80° C., and under atmospheric pressure or the pressure established according to the solvent and temperature. The sulfur compounds can be introduced into the solution all at once, in portions or continuously. After mixing in—if the desired decolorizing has not yet been achieved—the mixture is allowed to after-react at the temperature stated, while stirring, until the desired color quality and therefore the colorless solution sought exists. If colorless polyhydroxy-fatty acid amide as such is desired, it can be isolated and obtained from the solutions obtained according to the invention, for example by evaporating off or distilling off the solvent, in combination with filtration or centrifugation. The evaporative or distillative removal is preferably carried out at a temperature from 50° to 100° C. using a vacuum.

The polyhydroxy-fatty acid amide solutions obtained with the decolorizing process according to the invention and the polyhydroxy-fatty acid amide (powder, paste and the like) isolated therefrom, where appropriate, are practically colorless (water-clear). The good color quality is also retained during storage of the product. The products furthermore have a neutral odor, since because of the high activity of the dithionite compounds recommended, in general only a very small amount is required to achieve the bleaching sought. The process according to the invention thus leads to polyhydroxy-fatty acid amide products of good color quality, odor neutrality and a long-lasting stability toward discoloration or a change in color.

The invention is now explained in more detail by examples and comparison examples. The abbreviations NMG and GA used are N-methylglucamine and N-methylglucamide respectively.

EXAMPLE 1

1. Preparation of a GA solution by the process of the prior art:

97.6 g of NMG (0.5 mol) and 22 g of propylene glycol are initially introduced into a reaction vessel equipped with a stirrer, thermometer and reflux condenser and are heated to 125° C. 115.5 g (0.53 mol) of $C_{12}$ to $C_{14}$-fatty acid methyl ester and then 7.0 g of sodium methylate (that is 8 mol %, based on the NMG) are added at this temperature, after which the mixture is kept at a temperature of about 100° C. The methanol formed by the reaction is initially left in the system. When a degree of conversion of about 70% by weight of GA has been reached, a vacuum of 60 mbar is applied and the reaction is continued at a temperature of 85° to 88° C., the methanol being distilled off, until 92% by weight of GA, based on the solids content of the solution, has been formed after about 70 minutes. After removing the vacuum, the reaction mixture is taken up in 71.0 g of water and 33.0 g of ethanol. The resulting GA solution with water, propylene glycol and ethanol as the solvent is dark brown in color. It has a pH of 10 and the concentration of GA is 55% by weight. Two portions of about 130 g each are formed from this solution, and one of the two portions is brought to a pH of 8.3 with citric acid. Two dark brown-colored GA solutions having a pH of 10 [crude solution a)] and 8.3 [crude solution b)] thus exist.

2. Treatment according to the invention of the brown GA solutions a) and b):

The two crude solutions with in each case 130 g and with a GA concentration of 55% by weight are heated to 60° C. and in each case 0.13 g of solid sodium dithionite, that is 0.1% by weight of sodium dithionite, based on the weight of the solution, is added at this temperature, while stirring, after which the mixture is subsequently stirred at a temperature of about 60° C. for half an hour and then cooled. Solution a) is now likewise brought to a pH of 8.3 with citric acid.

The solutions a) and b) which now exist are—as can already be detected with the naked eye—virtually colorless. Furthermore, they have no odor relating to sulfur compounds. For a numerical illustration of the outstanding color quality of the two solutions bleached according to the invention, their light transmission values are determined and compared with the transmission value of the brown starting solution determined in the same manner. To determine the transmissions, a solution containing 25% by weight of GA is prepared using 50% strength by volume aqueous methanol and is measured at 420 nm in a 1 cm cell. The values thereby obtained are then converted to a 50% strength by weight GA solution. The results are summarized below:

Light transmission values:
  unbleached solution: 65.1% after the treatment according to the invention:
solution a): 79.8%
solution b): 77.6%

EXAMPLE 2

1. Preparation of $C_{12}$-N-methylglucamide by the process of the prior art:

219 g (1.0 mol) of $C_{12}$-fatty acid methyl ester are initially introduced into a reaction vessel and are heated to 100° C. 195 g (1.0 mol) of an NMG melt (130° C.) and 18 g of a 30% strength by weight methanolic sodium methylate solution (containing 0.1 mol) are now added in parallel under about 0.1 bar at 100° C. in the course of 1 hour. The methanol contained in the reaction mixture and constantly newly formed is removed continuously in vacuo, the viscosity of the mixture gradually rising. When removal of the solvent by distillation is complete, 9.4 g of citric acid are added, and a brown waxy product is thus finally obtained.

2. Treatment according to the invention of the glucamide thus obtained:

A solution of the resulting product containing 55% by weight of GA, 20% by weight of propylene glycol and 25% by weight of water is prepared at 60° C. and portions of this solution are treated with 0.05 or 0.2% by weight, based on the solution, of sodium dithionite at the same temperature for 1 hour. The cooled mixtures [(1): unbleached; (2): 0.05% by weight of dithionite; (3): 0.2% by weight of dithionite] have the following light transmission values (determined analogously to Example 1):

(1): 50.4%
(2): 71.4%
(3): 78.7%

The transmission can even be further increased significantly by storage at 40° C. for two weeks, while the untreated sample becomes darker:

(1): 48.5%
(2): 75.9%
(3): 89.5%

Comparison Example

For comparison of the bleaching action of, for example, sodium dithionite with that of other reducing sulfur compounds, in each case 0.1% by weight, based on the solution, of sodium dithionite (1), sodium sulfite (2) and sodium pyrosulfite (3) is added at 60° C. to the dark brown crude solution described in Example 2, which has a light transmission value of 50.4%, while stirring, after which the mixture is subsequently stirred at a temperature of about 60° C. for 1 hour and is then cooled. The light transmission values (determined analogously to Example 1) of the three bleached solutions (1), (2) and (3) are:

(1): 75.9%
(2): 63.1%
(3): 62.8%

The examples and comparison examples show the unexpectedly high bleaching action of the sulfur compounds recommended according to the invention, even when they are employed in only a very small amount.

We claim:

1. A process for preparing a solution, of improved color, of polyhydroxy-fatty acid amide from N-alkylpolyhydroxyamine and fatty acid alkyl ester, which comprises mixing at least one salt compound of the dithionous acid into the crude solution in an effective to improve the color thereof amount.

2. The process as claimed in claim 1, wherein an ammonium salt or alkali metal salt of dithionous acid in an active amount is mixed in.

3. The process as claimed in claim 1, wherein the salt compound is mixed in an amount of 0.005 to 1% by weight; the percentages by weight being based on the content of polyhydroxy-fatty acid amide in the crude solution.

4. The process as claimed in claim 1, wherein the mixing in is carried out at a temperature from 20 to 100° C.

5. The process as claimed in claim 2, wherein the salt compound is mixed in an amount of 0.05 to 0.15% by weight, the percentages by weight being based on the content of polyhydroxy-fatty acid amide in the crude solution.

6. The process as claimed in claim 5, wherein the mixing is carried out at a temperature from 40° to 80° C.

7. The process as claimed in claim 6, wherein the mixing is carried with a pH of 7 to 11.

8. The process as claimed in claim 1, wherein the solution contains 10 to 80% by weight polyhydroxy-fatty acid amide based on the weight of the solution.

9. The process as claimed in claim 10, wherein the solution contains 20 to 60% by weight polyhydroxy-fatty acid amide based on the weight of the solution.

10. A process for obtaining a polyhydroxy-fatty acid amide of approved color comprising isolating the polyhydroxy-fatty-acid amide from the solution as prepared according to claim 1.

* * * * *